United States Patent
Hasse et al.

(10) Patent No.: US 10,591,453 B2
(45) Date of Patent: Mar. 17, 2020

(54) TEST BENCH FOR SIMULATING THE ELECTRICAL RESPONSE OF A WIDEBAND LAMBDA SENSOR

(71) Applicant: dSPACE digital signal processing and control engineering GmbH, Paderborn (DE)

(72) Inventors: Dirk Hasse, Salzkotten (DE); Michael Wartig, Rheda-Wiedenbrueck (DE)

(73) Assignee: dSPACE digital signal processing and control engineering GmbH, Paderborn (DE)

( * ) Notice: Subject to any disclaimer, the term of this patent is extended or adjusted under 35 U.S.C. 154(b) by 333 days.

(21) Appl. No.: 15/841,848

(22) Filed: Dec. 14, 2017

(65) Prior Publication Data

US 2018/0164266 A1    Jun. 14, 2018

(30) Foreign Application Priority Data

Dec. 14, 2016    (DE) .................... 10 2016 124 328

(51) Int. Cl.
  *G01N 33/00*    (2006.01)
  *G01N 27/41*    (2006.01)
  (Continued)

(52) U.S. Cl.
  CPC ......... *G01N 33/0006* (2013.01); *G01N 27/41* (2013.01); *G01N 27/4163* (2013.01);
  (Continued)

(58) Field of Classification Search
  CPC . G01N 33/0006; G01N 27/41; G01N 27/4163
  (Continued)

(56) References Cited

U.S. PATENT DOCUMENTS 5,522,250 A    6/1996 Gee et al.
5,712,433 A    1/1998 Kojima
(Continued)

FOREIGN PATENT DOCUMENTS

CN    101793604 A    8/2010
CN    102656447 A    9/2012
(Continued)

OTHER PUBLICATIONS

Chinese First Office Action dated Jun. 13, 2018 in corresponding application 201711084901.3.
(Continued)

*Primary Examiner* — Tarun Sinha
(74) *Attorney, Agent, or Firm* — Muncy, Geissler, Olds & Lowe, P.C.

(57) ABSTRACT

A test bench for a control system for controlling a wideband lambda sensor, which is configured to calculate an actual value, which represents an oxygen concentration in a measuring gap of a wideband lambda sensor or an indicator value from which the oxygen concentration can be derived, with consideration of a current generated by a pump voltage in an electrical circuit. In order to simulate the electrical response of a pump cell of the wideband lambda sensor, a first diode and a second diode are connected in parallel in the electrical circuit such that a current flows through the first diode at a first polarity of the pump voltage and a current flows through the second diode at a second polarity of the pump voltage.

14 Claims, 3 Drawing Sheets

(51) Int. Cl.
*G01N 27/416* (2006.01)
*F02D 41/14* (2006.01)
*G01M 15/10* (2006.01)

(52) U.S. Cl.
CPC ...... *F02D 41/1456* (2013.01); *F02D 41/1495* (2013.01); *F02D 2041/1437* (2013.01); *G01M 15/104* (2013.01)

(58) Field of Classification Search
USPC .......................................................... 73/1.06
See application file for complete search history.

(56) References Cited

U.S. PATENT DOCUMENTS

| | | | |
|---|---|---|---|
| 8,029,656 | B2 | 10/2011 | Allmendinger |
| 9,880,127 | B2 | 1/2018 | Ledermann et al. |
| 2010/0100305 | A1 | 4/2010 | Bartick |
| 2010/0126883 | A1 | 5/2010 | Runge et al. |
| 2012/0266657 | A1 | 10/2012 | Barnikow et al. |
| 2013/0241429 | A1* | 9/2013 | Ruan ............ F02P 3/053 315/220 |
| 2014/0358355 | A1 | 12/2014 | Zimmerschied |
| 2015/0047411 | A1 | 2/2015 | Ledermann et al. |
| 2015/0204814 | A1 | 7/2015 | Ledermann et al. |

FOREIGN PATENT DOCUMENTS

| | | |
|---|---|---|
| CN | 102928471 A | 2/2013 |
| CN | 103257171 A | 8/2013 |
| CN | 104471411 A | 3/2015 |
| CN | 106150725 A | 11/2016 |
| DE | 196 31 922 A1 | 2/1997 |
| DE | 10 2006 062 056 A1 | 7/2008 |
| DE | 10 2006 062 057 A1 | 7/2008 |
| DE | 10 2007 061 947 A1 | 6/2009 |
| DE | 10 2011 077 353 A1 | 12/2012 |
| DE | 10 2011 089 383 A1 | 6/2013 |
| DE | 10 2012 201 767 A1 | 8/2013 |
| DE | 10 2012 213 068 A1 | 1/2014 |
| DE | 10 2013 221 298 A1 | 4/2014 |
| JP | 4045148 B2 | 3/2004 |
| JP | 2008045469 A | 2/2008 |
| KR | 20150069170 A | 6/2015 |

OTHER PUBLICATIONS

Oxygen Sensor Hack—You Tube Video—Veroeffentlicht—Jun. 5, 2016—https://www.youtube.com/watch.
Toyota 4Runner Forum—Largest 4Runner Forum—How to Make Your Own Rear O2 Simulator for $5—Aug. 8, 2014—http://toyota-4runner-org/3rd-gen-t4rs/175242-how-to -make-you-own-rear-o2-simulator.
Capristo Lambdasonde Simulator—YouTube Video Veroeffentlicht am Apr. 27, 2013—https://www.youtube.com/watch.
Capristo Lambda Similator Control Suite Manual—Dec. 3, 2012—http://www.capristo.de/upload/download/d_file_11.pdf.
SymTech Labs Intelligent Oxygen Sensor Simulator (iO2SS) Oct. 21, 2011—http://www.symtechlabs.com/support/docs/O2SimInstall3.pdf.
Oxygen Sensor Simulator—http://mkiv.com/techarticles/oxygen_sensor_simulator/index.html.
O2 Sensor Simultor—YouTube Video Veroeffentlicht am Nov. 21, 2012—https://www.youtube.com/watch.
AUTO DITEX BG Ltd., Automotive sensor simulator Operating Manual Nov. 4, 2016—http://autoditex.com/cms/user/fukes/autosimmanualen.pdf.
Marston, Ray, "555 Astable Circuits", Nuts & Volts Magazine—For the Electronics Hobbyist, Dec. 2000—http://www.nutsvolts.com/magazine/article/555-astable-circuits.
"A Few Words on Diode Clipper Distorsion",—Nov. 17, 2016—http://www.giangrandi.ch/electronics/diode-clipper/diode-clipper.shtml.
Configuration Desk IO Function Implementation Guide—Nov. 2015. DS2680 I/O unit (product description SCALEXIO, p. 23, subitem "Special I/O Channels", downloadable as a PDF at https://www.dspace.com/de/gmb/home/products/hw/simulator_hardware/scalexio.cfm).

* cited by examiner (State of the Art)

(State of the Art)

TEST BENCH FOR SIMULATING THE ELECTRICAL RESPONSE OF A WIDEBAND LAMBDA SENSOR

This nonprovisional application claims priority under 35 U.S.C. § 119(a) to German Patent Application No. 10 2016 124 328.0, which was filed in Germany on Dec. 14, 2016, and which is herein incorporated by reference.

BACKGROUND OF THE INVENTION

Field of the Invention

The present invention relates to the development of embedded systems for controlling wideband lambda sensors.

Description of the Background Art

Lambda sensors are used in internal combustion engines, e.g., motor vehicles with combustion engines, to monitor the combustion air ratio $\lambda$, a measure of the ratio of combustion air to fuel. Most lambda sensors are based on the measurement of a current of negatively charged oxygen ions through a hot zirconium dioxide layer. The simplest embodiment of a lambda sensor of this kind is known as a Nernst cell. The wideband lambda sensor is an expansion of the Nernst cell with a considerably larger measuring interval. It is formed substantially of two zirconium dioxide layers and a measuring gap arranged between these, which exchanges gas with the exhaust gas stream of the motor vehicle via a channel. Oxygen ions are transported from the exhaust gas into the measuring gap by means of a pump voltage, and the combustion air ratio in the measuring gap is thereby maintained at the balanced value $\lambda=1$. The pump current required for this is measured in order to draw a conclusion from it as to the combustion air ratio in the exhaust gas stream. A more detailed description of the function of a wideband lambda sensor is provided herein below.

A lambda sensor usually includes a control system, for example, an electronic control unit, for controlling and reading the lambda sensor. Automotive control systems typically undergo a complex development and evaluation process prior to their mass production, which also includes testing a prototype of the control system on a test bench. The test bench must be designed to simulate realistically the environment of the control system in real time, i.e., to read in control signals from the control system, to process and to generate input data expected from the control system, e.g. sensor values, plausibly and realistically, and to provide these to the control system. In the specific case, the control system must be able to apply a pump voltage to the test bench in order to produce a current (which is a pump current from the standpoint of the control system) and the test bench must calculate a value from the current, a value from which the control system can draw a conclusion on a combustion air ratio in a measuring gap.

It is known in the conventional art to apply the pump voltage of the control system to a simple resistor. An example of this can be found in the product description of the applicant's DS2680 I/O unit (product description SCALEXIO, page 23, subitem "Special I/O Channels", downloadable as a PDF at https://www.dspace.com/de/gmb/home/products/hw/simulator_hardware/scalexio.cfm). However, the current-voltage characteristic, hereinafter referred to as the electrical response, of an ohmic resistor is very different from the electrical response of an actual wideband lambda sensor. More recently, control devices for wideband lambda sensors are increasingly equipped with diagnostic functions which recognize this deviation of the electrical response and evaluate it as a fault. This is not compatible with the requirement of a realistic simulation of the environment, which is necessary for producing useful measuring results.

SUMMARY OF THE INVENTION

It is therefore an object of the invention to improve the plausibility of the electrical response to a pump voltage, applied by a control system for a wideband lambda sensor, in a test bench test.

In an exemplary embodiment, a test bench is provided for a control system configured to control a wideband lambda sensor. The test bench comprises an electrical circuit having a first terminal and a second terminal for application of a pump voltage, dropping across the electrical circuit, by the control system. Furthermore, the test bench is configured to calculate an actual value, which represents either an oxygen concentration in a measuring gap of a wideband lambda sensor, or an indicator value, which is expected by the control system and from which the oxygen concentration can be derived, with consideration of a current generated by the pump voltage in the electrical circuit. The indicator value can be in particular a diffusion voltage, dropping across a Nernst cell of the wideband lambda sensor, or a diffusion current flowing through the Nernst cell.

Furthermore, the test bench is configured to provide the actual value at a data output of the test bench, so that the actual value can be read out by the control system at the data output.

In the electrical circuit, a first diode and a second diode are connected in parallel such that a current flows through the first diode at a first polarity of the pump voltage and a current flows through the second diode at a second polarity of the pump voltage.

Thus, in an embodiment, the simple resistor for applying the pump voltage is replaced by a more complex electrical circuit, which comprises at least two diodes in the described arrangement. Even in this simple embodiment, the electrical circuit is suitable for simulating the electrical response of a wideband lambda sensor in a plausibly qualitative manner. In advantageous development stages of the invention, additional electrical components are added to the electrical circuit. Tests have shown that the electrical response of a specific wideband lambda sensor, available on the market or being developed, can also be simulated quantitatively by means of the additional components, so that a fault-free and realistic test of the control system is possible even in the case of high requirements by the control system of the specific wideband lambda sensor for the plausibility of the electrical response to the pump current.

In an embodiment, a first electrical resistor is connected in series to the first diode, and a second resistor is connected in series to the second but not to the first diode. The slope of the electrical response can be influenced for very high or very low $\lambda$ values by means of the first resistor and second resistor.

In an embodiment, a capacitor is connected in parallel to the first and second diode in order to simulate a parasitic capacitance of a zirconium dioxide layer of the wideband lambda sensor.

In an embodiment, a third resistor is connected in series to the first diode and the second diode, and in particular also connected in series to the capacitor. Particularly advantageously, the third resistor can be a controllable resistor in order to simulate the temperature dependence of the electrical conductivity of a zirconium dioxide layer. The test bench can then be configured to assign a temperature to a pump cell of a wideband lambda sensor, for example, by means of a software model, to assign an electrical resistance of the pump cell to the temperature based on a characteristic curve, and to adjust the electrical resistance of the controllable resistor to the electrical resistance associated with the temperature.

A pump cell can be understood to be a zirconium dioxide layer of a wideband lambda sensor, which is configured and provided to be placed between the measuring gap and an exhaust gas stream in order to exchange oxygen ions between the exhaust gas stream and the measuring gap. The electrical circuit is provided to simulate the electrical response of the pump cell.

In an embodiment, the test bench also comprises a control system, which is configured to control a wideband lambda sensor and is configured to read out the actual value from the data output, to apply the pump voltage to the first terminal and the second terminal, and to adjust the actual value to a set value stored in the control system by controlling the pump voltage. The control system is, for example, integrated as a unit under test into the test bench and is, for example, a prototype which is to be tested for error-free function by means of the test bench. The unit under test is then configured to read in the actual value, in the normal case the voltage dropping across the Nernst cell, and to use it as an indicator for the combustion air ratio $\lambda$ in the measuring gap. Furthermore, it is configured to influence the combustion air ratio $\lambda$ in the measuring gap by controlling the pump voltage and to adjust the actual value to a set value stored in the control system.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
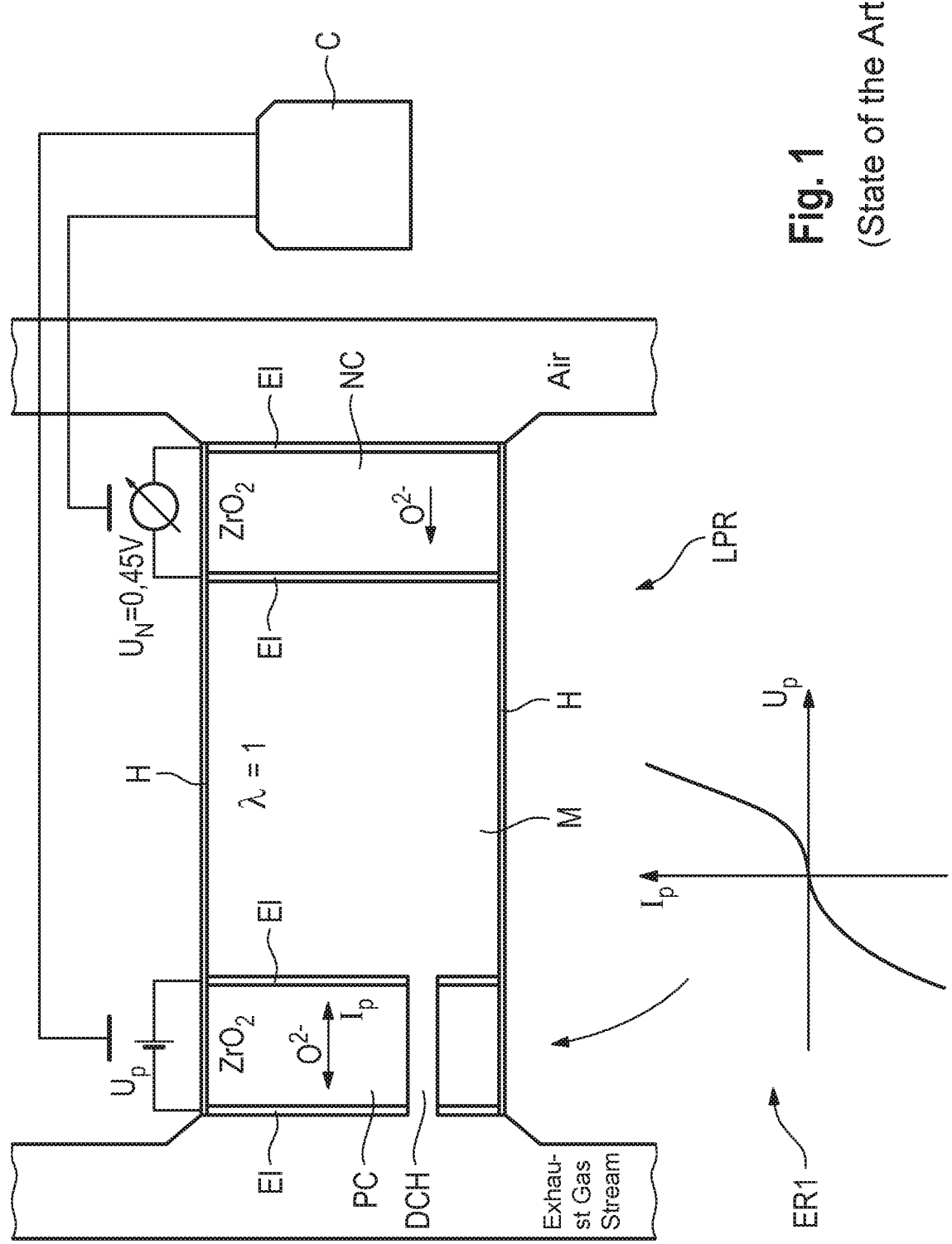
FIG. 1 shows a diagram of a typical wideband lambda sensor with a control system and the electrical response of the pump cell of the wideband lambda sensor.

The illustration in FIG. 1 shows a typical wideband lambda sensor LPR, installed in a motor vehicle, with a control system C for controlling the wideband lambda sensor LPR. Control system C is designed as an electronic control unit. The wideband lambda sensor comprises two membranes PC, NC made of zirconium dioxide (ZrO2), between which a gas-filled measuring gap M is located. Both membranes are coated on both sides with gas-permeable electrodes El.

One of the membranes is referred to as the pump cell PC and the other membrane as the Nernst cell NC. Wideband lambda sensor LPR is placed in the motor vehicle in such a way that electrode El, externally adjacent to pump cell PC, is located in the motor vehicle exhaust gas stream and electrode El, externally adjacent to Nernst cell NC, is located at the outside air. The outside air is routed, for example, to the wideband lambda sensor LPR by means of a line. Zirconium dioxide is conductive for negatively ionized oxygen starting at a temperature of about 300° C. and above. In order to quickly bring wideband lambda sensor LPR to the operating temperature after the motor vehicle is started, it is equipped with two heating plates H.

Measuring gap M exchanges gas with the exhaust gas stream via a diffusion channel DCH driven by pump cell PC. Accordingly, when the wideband lambda sensor LPR is turned off, the oxygen concentration in measuring gap M would conform to the oxygen concentration in the exhaust gas stream. The oxygen concentration is characterized by the combustion air ratio $\lambda$, where a value $\lambda=1$ represents a balanced ratio of oxygen and fuel. A value $\lambda>1$ indicates an oxygen excess ("lean mixture") and a value $\lambda<1$ a fuel excess ("rich mixture").

Oxygen atoms are ionized at electrodes El, and the ions can then diffuse through pump cell PC or Nernst cell NC. Because of the higher oxygen content in the ambient air, a diffusion voltage $U_N$, dropping across Nernst cell NC, builds up and can be used as an indicator value for the combustion air ratio $\lambda$ in measuring gap M; i.e., a conclusion on the combustion air ratio $\lambda$ in the measuring gap can be drawn directly from the diffusion voltage $U_N$. For example, a diffusion voltage of the magnitude UN=0.450 V is evaluated as a balanced combustion air ratio $\lambda=1$. Control system C is configured to measure the diffusion voltage $U_N$ and to read in the measured diffusion voltage $U_N$.

Control system C is also configured to apply a pump voltage $U_p$, dropping across pump cell PC, to pump cell PC. Pump voltage $U_p$ generates a pumping current $I_P$ of oxygen ions through the pump cell depending on the polarity from the exhaust gas stream into measuring gap M or vice versa, and thereby influences the value of $\lambda$ in the measuring gap. The control system is configured to measure diffusion voltage $U_N$ and to maintain a balanced combustion air ratio $\lambda=1$ by controlling pump voltage $U_p$ in the measuring gap in that control system C adjusts the diffusion voltage to the value $U_N=0.450$ V. Control system C derives the value of $\lambda$ in the exhaust gas stream from pump current $I_P$ required for this purpose, which control system C is likewise configured to measure.

The illustration also shows in a qualitative diagram a first electrical response ER1 of pump cell PC, i.e., the characteristic curve of pump cell PC which plots pump current $I_P$ versus pump voltage $U_p$. The first electrical response ER1 is not symmetric to the origin because the formation of oxygen ions at electrodes El is based on different chemical processes, depending on the flow direction of pump current $I_P$. In the case of a flow direction from the exhaust gas stream into the measuring gap, the oxygen ions are mainly formed from water molecules, and in the case of the opposite flow direction mainly from oxygen molecules.

Figure 2:
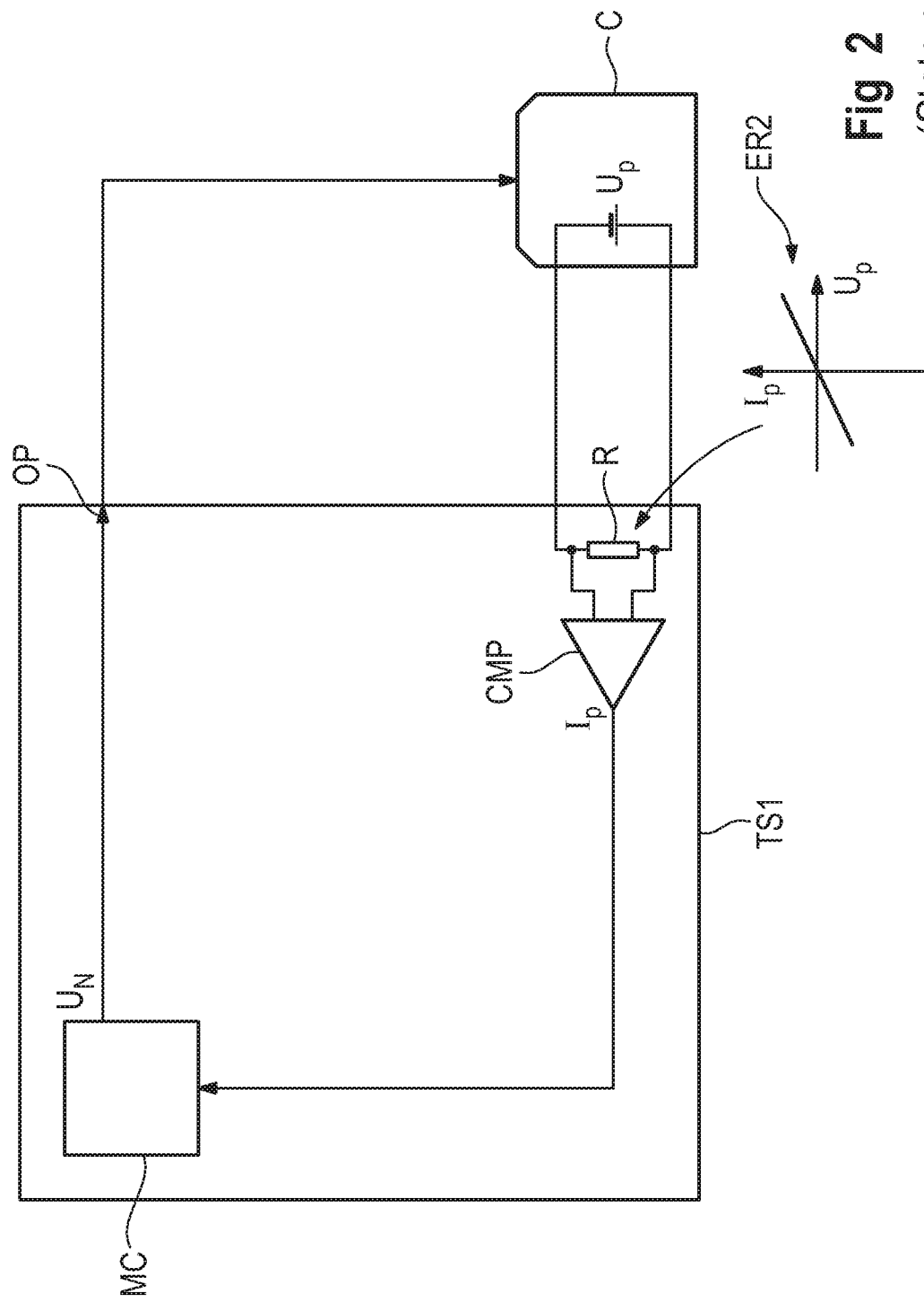
FIG. 2 shows a test bench known from the conventional art for testing a control system of a wideband lambda sensor.

The diagram in FIG. 2 shows a first test bench TS1 for control system C, as it is known from the prior art. First test bench TS1 comprises a resistor R to which control system C applies pump voltage $U_p$ instead of to pump cell PC. A differential amplifier CMP is configured to measure pump current $I_P$ flowing through resistor R. First test bench TS1 also comprises a processor MC which is configured to read the pump current $I_P$ from differential amplifier CMP in order to calculate a value for the diffusion voltage $U_N$ by means of a software model stored in processor MC, taking pump current $I_P$ into account, and to provide the value of diffusion voltage $U_N$ at a data output OP of first test bench TS1. Control system C is configured to read the value of diffusion voltage $U_N$ from data output OP.

The software model in processor MC is a simulation of the environment of control system C. To calculate diffusion voltage $U_N$, in addition to pump current $I_P$, it takes into account further variables which are either calculated by the software model or supplied by physical components of first test bench TS1, for example, those of real loads or of additional components of first test bench TS1 which are configured for the sensor simulation. In particular, the software model includes a simulation of a wideband lambda sensor LPR and a simulation of the exhaust gas stream, which specifies a value for the oxygen concentration in the exhaust gas stream. In principle, the software model can be designed with any complexity and may include, for example, a simulation of a combustion engine, in addition further components of a virtual motor vehicle, and a virtual environment of the virtual motor vehicle in which the virtual motor vehicle performs driving maneuvers. Pump current $I_P$ measured by differential amplifier CMP is interpreted by the software model as a pump current of oxygen ions through a pump cell PC of the simulated wideband lambda sensor LPR.

First test bench TS1 is thus configured to simulate the operation in a motor vehicle for control system C. Control system C applies a pump voltage $U_p$ and receives, as a response, a simulated diffusion voltage $U_N$ which is calculated by first test bench TS1 by simulating a wideband lambda sensor LPR in the software model and is controllable by controlling pump voltage $U_p$ by means of control system C.

The electrical response of resistor R is shown as the second electrical response ER2. A disadvantage of first test bench TS1 is that the second electrical response ER2 is a line through the origin, which therefore differs from the first electrical response ER1. If control system C comprises a diagnostic function for checking the plausibility of second electrical response ER2, this leads to an error message of control system C.

Figure 3:
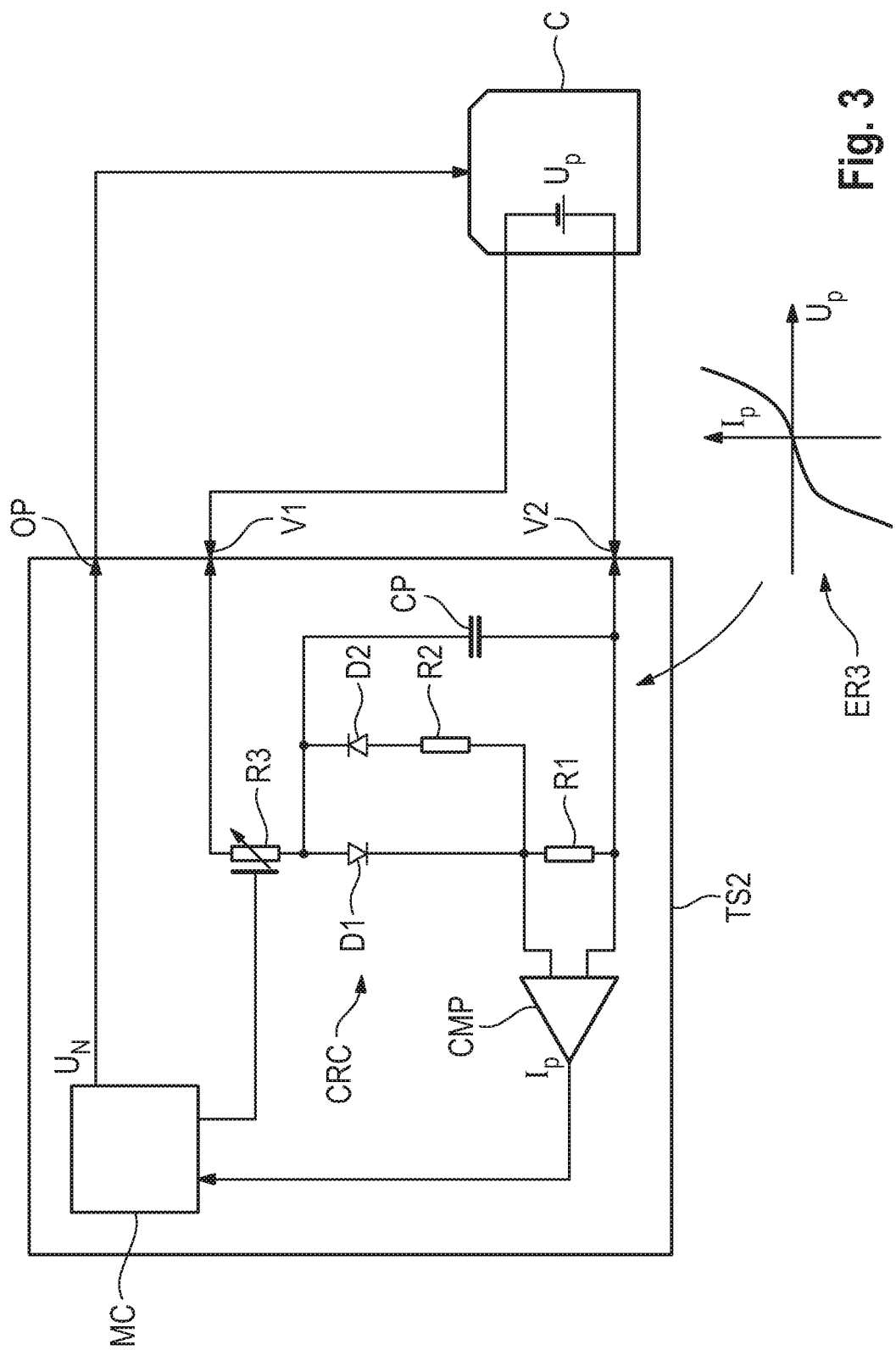
FIG. 3 shows a test bench of the invention for testing a control system of a wideband lambda sensor according to an exemplary embodiment.

The illustration in FIG. 3 shows a second test bench TS2, which implements an advantageous embodiment of the invention. In second test bench TS2, resistor R is replaced by an electrical circuit CRC, by means of which the electrical response ER1 of pump cell PC of a wideband lambda sensor LPR, for example, the first electrical response ER1, can be quantitatively simulated. Only the differences from FIG. 2 will be explained below. Components which are given the same reference characters in FIG. 2 and FIG. 3 are assumed to be of identical design.

Test bench TS2 comprises a first terminal V1 and a second terminal V2 for applying a pump voltage dropping across electrical circuit CRC, and control system C is connected to first terminal V1 and second terminal V2 in such a way that pump voltage $U_p$, applied by control system C, drops across electrical circuit CRC. The electrical response of electrical circuit CRC, represented by a third electrical response ER3, is a simulation of the electrical response of pump cell PC of a wideband lambda sensor LPR, for example, the first electrical response ER1.

In electrical circuit CRC, a first diode D1 and a second diode D2 are connected in parallel with the opposite conducting direction, so that, depending on the polarity of pump voltage $U_p$, the pump current flows either through first diode D1 but not through second diode D2 or the pump current flows through second diode D2 but not through first diode D1. A qualitative simulation of the first electrical response ER1 is already achieved solely by this arrangement of first diode D1 and second diode D2.

A first resistor R1 is connected in series to first diode D1, and first resistor R1 and a second resistor R2 are connected in series to second diode D2. First resistor R1 and second resistor R2 influence the slope of third electrical response ER3 for strongly positive and strongly negative values of pump voltage $U_p$ outside the diode drop in the vicinity of UP=0. Tests have shown that, by clever selection of first diode D1, second diode D2, first resistor R1, and second resistor R2, the electrical response of the pump cell of a specific wideband lambda sensor can also be simulated quantitatively with a high accuracy, so that within the total spectrum, controlled by control system C, of pump voltage $U_p$, pump current $I_P$ through electrical circuit CRC corresponds with a high accuracy to pump current $I_P$ through pump cell PC of the specific wideband lambda sensor LPR. For this purpose, the electrical response of the pump cell of the specific wideband lambda sensor is measured before the selection of the noted components.

To simulate further aspects of the electrical response of pump cell PC, the electrical circuit additionally comprises a capacitance in the form of a capacitor CP and a controllable third resistor R3. Capacitor CP is connected in parallel to first diode D1, second diode D2, first resistor R1, and second resistor R2 and simulates a parasitic capacitance of pump cell PC. The capacitance of capacitor CP in this case is selected to be the same or similar to the parasitic capacitance of the pump cell of the specific wideband lambda sensor.

Third resistor R3 is connected in series to first diode D1, second diode D2, first resistor R1, second resistor R2, and capacitor CP and simulates a temperature dependency of the electrical resistance of pump cell PC. For this purpose, in order to control third resistor R3, processor MC is configured to assign a temperature to a pump cell PC of the simulated wideband lambda sensor by reading the temperature from a memory address or by calculating it using the software model, to assign an electrical resistance of pump cell PC to the temperature based on a characteristic curve stored in a memory of test bench TS2, and to adjust the electrical resistance of third resistor R3 to the electrical resistance associated with the temperature. For this purpose, for example, a combustion engine simulation contained in the software model can calculate a temperature of the exhaust gas stream and can calculate a temperature of the pump cell from the temperature of the exhaust gas stream using a heat conduction model.

Differential amplifier CMP is set up to measure the current flowing through first resistor R1. This arrangement of differential amplifier CMP has the advantage that, for the measurement of pump current $I_P$, only the current which corresponds to the pump current through pump cell PC and flows through first diode D1 or second diode D2, is taken into account, whereas the current flowing through capacitor CP is not taken into account.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A test bench for a control system configured to control a wideband lambda sensor, the test bench having an electrical circuit comprising:
   a first terminal; and
   a second terminal, a pump voltage is applied by the control system such that a drop across the electrical circuit is caused,
   wherein the test bench is configured to calculate an actual value, which represents an oxygen concentration in a measuring gap of a wideband lambda sensor or an indicator value from which the oxygen concentration is derived based on a current generated by the pump voltage in the electric circuit,
   wherein the test bench provides the actual value at a data output of the test bench so that the actual value is read out by the control system, and
   wherein, in the electrical circuit, a first diode and a second diode are connected in parallel such that a current flows through the first diode at a first polarity of the pump voltage and a current flows through the second diode at a second polarity of the pump voltage.

2. The test bench according to claim 1, wherein the indicator value is: a diffusion voltage dropping across a Nernst cell of the wideband lambda sensor, or an electrical diffusion current flowing through the Nernst cell.

3. The test bench according to claim 1, wherein the electrical circuit further comprises a first resistor connected in series to the first diode, and a second resistor connected in series to the second diode but not to the first diode.

4. The test bench according to claim 1, wherein the electrical circuit further comprises a capacitor connected in parallel to the first diode and the second diode.

5. The test bench according to claim 1, wherein the electrical circuit comprises a third resistor connected in series to the first diode and the second diode.

6. The test bench according to claim 5, wherein the third resistor is a controllable resistor.

7. The test bench according to claim 6, wherein the test bench is configured: to control the third resistor to assign a temperature to a pump cell of the wideband lambda sensor, to assign an electrical resistance of the pump cell to the temperature based on a characteristic curve stored in a memory of the test bench, and/or to adjust the electrical resistance of the third resistor to the electrical resistance associated with the temperature.

8. The test bench according to claim 1, wherein the control system is configured: to control a wideband lambda sensor and is configured to read out the actual value from the data output, to apply the pump voltage to the first terminal and the second terminal, and/or to adjust the actual value to a set value stored in the control system by controlling the pump voltage.

9. A test method for a control system configured to control a broadband lambda sensor, the method comprising:
   connecting the control system to an electrical circuit such that a pump voltage, which is controlled by the control system and is provided for application to a pump cell of the wideband lambda sensor, drops across the electrical circuit;
   calculating, based on the pump voltage, an actual value that represents an oxygen concentration in a measuring gap of a wideband lambda sensor or an indicator value from which the oxygen concentration is derived; and
   connecting, in the electrical circuit, a first diode and a second diode in parallel such that a current flows through the first diode at a first polarity of the pump voltage and a current flows through the second diode at a second polarity of the pump voltage.

10. The test method according to claim 9, wherein a first resistor is connected in series to the first diode, and wherein a second resistor is connected in series to the second diode but not to the first diode.

11. The test method according to claim 10, wherein the electrical response of the pump cell of a broadband lambda sensor is measured, and wherein the first diode, the second diode, the first resistor, and the second resistor are selected so that an electrical response of the electrical circuit quantitatively simulates the electrical response of the pump cell.

12. The test method according to claim 9, wherein a capacitor is connected in parallel to the first diode and the second diode.

13. The test method according to claim 9, wherein the control system is configured to adjust the actual value to a set value by controlling the pump voltage, and wherein the control system is configured to read out the actual value.

14. The test method according to claim 9, wherein a controllable resistor is connected in series to the first diode and to the second diode, wherein a temperature is assigned to a pump cell of the wideband lambda sensor, wherein an electrical resistance of the pump cell is assigned to the temperature using a characteristic curve, and wherein the electrical resistance of the controllable resistor is adjusted to the electrical resistance associated with the temperature.

* * * * *